United States Patent
Geck et al.

(10) Patent No.: US 9,752,508 B2
(45) Date of Patent: Sep. 5, 2017

(54) AIR TURBINE STARTERS HAVING OIL FEED SHUTOFF VALVES AND GAS TURBINE ENGINES INCLUDING THE SAME

(71) Applicant: HONEYWELL INTERNATIONAL INC., Morristown, NJ (US)

(72) Inventors: Kellan Geck, Chandler, AZ (US); Gerhard Schroeder, Phoenix, AZ (US); Doug Smith, Phoenix, AZ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 230 days.

(21) Appl. No.: 14/755,668

(22) Filed: Jun. 30, 2015

(65) Prior Publication Data

US 2015/0292414 A1    Oct. 15, 2015

Related U.S. Application Data

(60) Provisional application No. 62/151,552, filed on Apr. 23, 2015.

(51) Int. Cl.
| | |
|---|---|
| *F02C 7/27* | (2006.01) |
| *F02C 7/275* | (2006.01) |
| *F02C 7/277* | (2006.01) |
| *A61F 2/16* | (2006.01) |

(52) U.S. Cl.
CPC .............. *F02C 7/27* (2013.01); *A61F 2/1613* (2013.01); *A61F 2/1629* (2013.01); *A61F 2/1648* (2013.01); *A61F 2/1694* (2013.01); *F02C 7/275* (2013.01); *F02C 7/277* (2013.01)

(58) Field of Classification Search
CPC .... F02C 7/06; F02C 7/27; F02C 7/275; F02C 7/277; F02C 7/32; F02C 7/26
See application file for complete search history.

(56) References Cited

U.S. PATENT DOCUMENTS

| | | |
|---|---|---|
| 6,681,579 B2 | 1/2004 | Lane et al. |
| 7,014,419 B2 | 3/2006 | Farnsworth et al. |
| 7,033,133 B2 | 4/2006 | Bristol et al. |

(Continued)

FOREIGN PATENT DOCUMENTS

WO    03067053 A2    8/2003

OTHER PUBLICATIONS

Extended EP Search Report for Application No. 16164986.8 dated Sep. 16, 2016.

*Primary Examiner* — Steven Sutherland
(74) *Attorney, Agent, or Firm* — Lorenz & Kopf, LLP

(57) ABSTRACT

Air Turbine Starters (ATSs) having oil feed shutoff valves are provided, as are gas turbine engines including ATSs. In one embodiment, the ATS includes an ATS housing assembly containing a sump chamber, an oil inlet, and a valve cavity. A rejected oil return passage is further formed in the ATS housing assembly and fluidly coupled to the valve cavity. An oil feed shutoff valve is positioned in the valve cavity and contains a valve element movable between open and closed positions. In the open position, the valve element permits oil flow from the oil inlet, through the valve cavity, and into the sump chamber. In the closed position, valve element blocks oil flow from the oil inlet into the sump chamber, while redirecting the oil flow into rejected oil return passage to reduce the loss of engine oil through the ATS in the event of an ATS housing breach.

20 Claims, 3 Drawing Sheets

(56) References Cited

U.S. PATENT DOCUMENTS

| | | |
|---|---|---|
| 7,033,134 B2 | 4/2006 | Bristol et al. |
| 7,367,427 B2 | 5/2008 | Gaines et al. |
| 2005/0186067 A1 | 8/2005 | Bristol et al. |
| 2006/0056958 A1 | 3/2006 | Gaines et al. |
| 2003/8000309 | 1/2008 | Giesler et al. |
| 2014/0250914 A1* | 9/2014 | Slayter .................. F02C 7/277 60/787 |
| 2015/0082805 A1 | 3/2015 | Zeiner et al. |

* cited by examiner

AIR TURBINE STARTERS HAVING OIL FEED SHUTOFF VALVES AND GAS TURBINE ENGINES INCLUDING THE SAME

CROSS-REFERENCE TO RELATED APPLICATION

This application claims the benefit of U.S. Provisional Application No. 62/151,552, filed with the USPTO on Apr. 23, 2015.

TECHNICAL FIELD

The present invention relates generally to air-started gas turbine engines and, more particularly, to embodiments of an air turbine starter having an oil feed shutoff valve, which minimizes engine oil loss in the event of starter breach.

BACKGROUND

An Air Turbine Starter (ATS) is utilized to initiate Main Engine Start (MES) of a gas turbine engine. The ATS is commonly implemented as a Line Replaceable Unit (LRU) installed on the Accessory Gearbox (AGB) of the engine. By common design, an ATS includes a lubrication system, which maintains the rotating components of the ATS in a lubricated state during operation of the ATS. The lubrication system can be self-contained such that the ATS does not exchange oil with the larger gas turbine engine. Alternatively, the ATS may have a "shared oil" lubrication system enabling circulation of the engine oil through the ATS. The engine oil is typically conditioned (e.g., filtered, pressurized, and/or cooled) and thus maintained at a relatively high quality during the lifespan of the engine. Thus, by allowing the ATS to take advantage of this high quality oil supply, a shared oil lubrication system can prolong the service life and improve the overall reliability of the ATS.

While providing the above-noted benefits, equipping an ATS with a shared lubrication system also presents certain challenges. For example, in the unlikely event of an ATS housing breach (that is, a compromise in the sealed environment of the ATS), the engine oil circulated through the ATS can rapidly escape to the surrounding environment as liquid or vapor (oil trapped in air) due to the pressure differential between the ATS housing and its surrounding environment. If a significant volume of engine oil is lost through the ATS, inflight shutdown of the gas turbine engine may be necessitated. To help reduce the loss of engine oil through the ATS in the event of a housing breach, the ATS may be further equipped with an oil feed shutoff valve. The oil feed shutoff valve may typically reside in an open position under normal operational conditions. However, if an ATS housing breach should occur, the oil feed shutoff valve closes to impede the flow of engine oil into the ATS thereby effectively sequestering the leak and preventing significant oil loss through the ATS.

While serving as a useful oil loss control feature in the context of a shared oil ATS, conventional oil feed shutoff valves remain limited in certain respects. For example, as conventionally proposed, an oil feed shutoff valve may not provide a complete seal when closed. As a result, engine oil may still be permitted to flow into the ATS and escape to the external environment (e.g., the interior of nacelle) in the event of an ATS housing breach. Furthermore, even when equipped with an oil feed shutoff valve, a conventional ATS may lack an effective means for relieving the accumulation of oil pressure behind the shutoff valve when closed. As a result, undesired pressure build-up or "dead heading" of the engine oil may occur upstream of the shutoff valve further exacerbating oil leakage into the ATS under breach conditions. Finally, as a still further limitation, conventional ATS designs may permit undesired oil drainage back the AGB when the oil feed shutoff valve is in a fully or partially open position.

It is thus desirable to provide embodiments of a shared oil ATS including an oil feed shutoff valve, which overcomes one or more of the above-mentioned limitations. For example, it is desirable to provide a shared oil ATS having an oil feed shutoff valve, which achieves a high integrity seal when in a closed position to greatly reduce, if not entirely prevent the inflow of engine oil into the ATS under breach conditions. It is also desirable for such an ATS to alleviate the accumulation of oil pressure upstream of the shutoff valve when closed; and/or to prevent the undesired drainage of oil when the shutoff valve is in an open or partially open position. Finally, it is desirable to provide embodiments of a gas turbine engine including an ATS providing such performance characteristics. Other desirable features and characteristics of embodiments of the present invention will become apparent from the subsequent Detailed Description and the appended Claims, taken in conjunction with the accompanying drawings and the foregoing Background.

BRIEF SUMMARY

Air Turbine Starters (ATSs) having oil feed shutoff valves are provided. In one embodiment, the ATS includes an ATS housing assembly containing a sump chamber, an oil inlet, and a valve cavity fluidly coupled between the sump chamber and the oil inlet. A rejected oil return passage is further formed in the ATS housing assembly and fluidly coupled to the valve cavity. An oil feed shutoff valve is positioned in the valve cavity and contains a valve element movable between open and closed positions. The valve element normally resides in the open position and transitions to the closed position under breach conditions. In the open position, the valve element permits oil flow from the oil inlet, through the valve cavity, and into the sump chamber of the ATS. In the closed position, the valve element blocks oil flow from the oil inlet into the sump chamber, while redirecting the oil flow into rejected oil return passage to reduce the loss of engine oil through the ATS in the event of an ATS housing breach.

In a further embodiment, the ATS includes an ATS housing assembly containing a sump chamber and an oil inlet. A valve cavity is fluidly coupled between the sump chamber and the oil inlet, and a circumferential groove extends at least partially around the valve cavity. An oil feed shutoff valve is positioned in the valve cavity and contains a valve element having an annular sidewall. The oil feed shutoff valve is movable between open and closed positions in which the annular sidewall uncovers and covers the circumferential groove, respectively, to selectively block or impede oil flow from the oil inlet, through the circumferential groove, and into the sump chamber. In this manner, the oil feed shutoff valve can be moved into the closed position to block, in whole or in substantial part, the inflow of engine oil into the ATS under breach conditions.

Embodiments of a gas turbine engine are further provided. In one embodiment, the gas turbine includes an Accessory Gearbox (AGB) and an ATS, which is fluidly coupled to the AGB and configured to exchange oil therewith during operation of the gas turbine engine. The ATS includes, in turn, an ATS housing assembly containing a sump chamber, an oil inlet, and a valve cavity fluidly coupled between the sump chamber and the oil inlet. A rejected oil return passage is further formed in the ATS housing assembly and fluidly coupled to the valve cavity. An oil feed shutoff valve is positioned in the valve cavity and contains a valve element movable between open and closed positions. In the open position, the valve element permits oil flow from the oil inlet, through the valve cavity, and into the sump chamber of the ATS. In the closed position, valve element blocks oil flow from the oil inlet into the sump chamber, while redirecting the oil flow into rejected oil return passage to reduce the loss of engine oil through the ATS in the event of an ATS housing breach.

BRIEF DESCRIPTION OF THE DRAWINGS

At least one example of the present invention will hereinafter be described in conjunction with the following figures, wherein like numerals denote like elements, and.

DETAILED DESCRIPTION

The following Detailed Description is merely exemplary in nature and is not intended to limit the invention or the application and uses of the invention. Furthermore, there is no intention to be bound by any theory presented in the preceding Background or the following Detailed Description.

Figure 1:
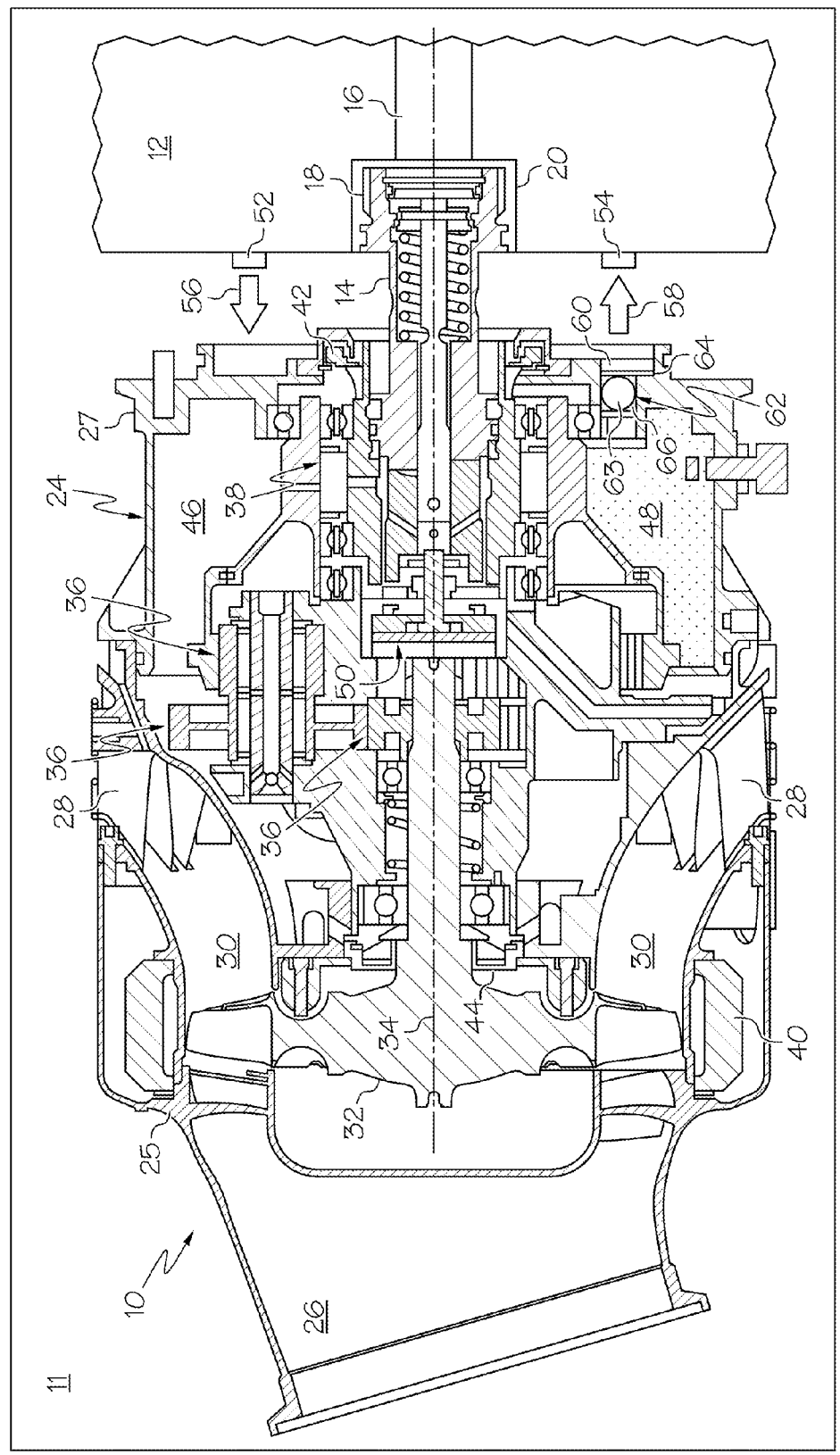
FIG. 1 is a cross-sectional view of a shared oil Air Turbine Starter (ATS) including an oil feed shutoff valve (hidden from view in FIG. 1) and installed within a gas turbine engine (schematically shown), as illustrated in accordance with an exemplary embodiment of the present invention.

FIG. 1 is a cross-sectional view of a shared oil Air Turbine Starter (ATS) 10, as illustrated in accordance with an exemplary embodiment of the present invention. ATS 10 is included within a larger Gas Turbine Engine (GTE) 11, which is generically represented by a box symbol in FIG. 1. GTE 11 further includes an Accessory Gearbox (AGB) 12 (schematically shown) and an engine core containing one or more spools (not shown). ATS 10 is preferably implemented as a Line Replaceable Unit (LRU), which is installed on AGB 12 and can be readily removed therefrom to facilitate in-field replacement or repair. Specifically, ATS 10 may be installed on a support surface or "pad" of AGB 12, which may include additional pads supporting other LRUs (not shown). When ATS 10 is installed on AGB 12, an output shaft 14 of ATS 10 matingly engages a mechanical input 16 of AGB 12 to provide a rotationally fixed coupling therebetween. For example, as generically indicated in FIG. 1, ATS output shaft 14 can include a splined male interface 18, which mates with a splined female interface 20 of AGB input 16. Gearing contained within AGB 12 mechanically links ATS output shaft 14 to the non-illustrated engine spool or spools to enable ATS 10 to drive rotation of the engine core during Main Engine Starter (MES) of GTE 11.

Shared oil ATS 10 includes a main housing assembly 24, which can assume any form and may be produced from any number of components suitable for containing or otherwise supporting the various components of ATS 10. In the illustrated exemplary embodiment, main housing assembly 24 includes an exhaust housing portion 25 and gearbox housing portion 27. An airflow inlet 26, an airflow outlet 28, and a connecting flow passage 30 are formed in exhaust housing portion 25 of ATS 10. Specifically, airflow inlet 26 is provided in a first end of exhaust housing portion 25, while airflow outlet 28 is formed around a second end of exhaust housing portion 25. Flow passage 30 fluidly couples airflow inlet 26 to airflow outlet 28 and has a substantially conical geometry, it being understood that many of the ATS components are generally axisymmetric about the centerline or rotational axis of ATS 10 (represented by dashed line 34). An air turbine 32 is further disposed within exhaust housing portion 25 and positioned such that the turbine blades project radially into conical flow passage 30. Air turbine 32 is rotatable relative to housing assembly 24 about rotational axis 34. Air turbine 32 is mechanically linked to ATS output shaft 14 through a planetary gear train 36 and a unidirectional (e.g., spray) clutch 38, which are each contained within gearbox housing portion 27 of housing assembly 24. Planetary gear train 36 provides a desired gear reduction between air turbine 32 and ATS output shaft 14, while unidirectional clutch 38 prevents the undesired back-driving of air turbine 32 after MES of GTE 11. Shared oil ATS 10 further includes various additional components, which will not be described in detail to avoid unnecessarily obscuring the invention. Such additional components can include a number of rolling element bearings supporting the various rotating components of ATS 10, a containment ring 40 circumscribing air turbine 32, an output shaft seal 42 disposed around ATS output shaft 14, and a turbine seal 44 disposed around the shaft section of air turbine 32.

A sealed internal compartment or sump chamber 46, 48 is provided within gearbox housing portion 27 of ATS housing assembly 24. ATS sump chamber 46, 48 includes an air cavity 46 and an underlying sump 48, which holds a certain volume or reservoir of the engine oil circulated through shared oil ATS 10 (represented by cross-hatching in FIG. 1). A shaft-driven pump 50 draws oil from sump 48 and directs the oil into one or more of the rotating components of ATS 10, such as clutch 38 and planetary gear train 36. During operation, ATS 10 may continually receive a supply of engine oil from AGB 12, which may be provided as a metered supply, a continuous spray, or another type of stream whether gravity fed or pressurized. This may be appreciated by continued reference to FIG. 1 wherein the oil outlet and inlets of AGB 12 are generically represented by symbols 52 and 54, respectively; and the direction of oil flow between AGB 12 and ATS 10 is represented by arrows 56 and 58 (also representative of the flow lines or conduits connecting AGB 12 and ATS 10). As can be seen, the oil outlet of ATS 10 is located in the lower right corner of the drawing figure and identified by reference numeral "60." The oil inlet of ATS 10 is hidden from view in FIG. 1 due to the location of the cross-section, but is generally located above the plane of the page to the immediate left of arrow 56 in the drawing figure. The oil inlet of shared oil ATS 10 is, however, shown in FIGS. 2-3 and will be described more fully below in conjunction therewith.

If not equipped with adequate oil loss control features, shared oil ATS 10 can permit the rapid escape of engine oil to the surrounding environment (e.g., the interior of the engine nacelle) in the unlikely event of an ATS housing breach; as appearing herein, the term "ATS housing breach" referring to any compromise in the sealed environment of housing assembly 24 permitting leakage of oil from ATS sump chamber 46, 48. An ATS housing breach can occur if ATS output shaft seal 42 should fail or ATS housing assembly 24 should fracture due to, for example, detachment of rotating component (e.g., a turbine blade) when rotating at a high rate of speed. In the exemplary embodiment illustrated in FIG. 1, ATS 10 is equipped with at least three such oil loss control features. First, ATS output shaft seal 42 is considered an oil loss control feature in that seal 42 help prevents the outflow of oil from sump chamber 46, 48 should an ATS housing breach occur. Second, shared oil ATS 10 is equipped with an oil outflow check valve 62 (shown in the lower right corner of FIG. 1) disposed immediately upstream of ATS oil outlet 60. In the illustrated example, oil outflow check valve 62 contains a spherical valve element 63, which is normally maintained against a screen 64 by the pressure head of oil contained within sump 48. As the oil level of sump 48 decreases in conjunction with oil leakage from ATS 10, so too does the force applied against valve element 63 in the direction of screen 64 by the pressure head of the oil reservoir. Valve element 63 will consequently slide away from screen 64 (to the left in FIG. 1), contact valve seat 66, and impede the inflow of oil into outlet 60 of ATS 10 from AGB 12 in a direction opposite arrow 58. Check valve 62 thus closes to prevent further withdrawal of engine oil from GTE 11 through AGB inlet 54 in the event of an ATS housing breach. As a third oil loss control feature, ATS 10 is further equipped with an oil feed shutoff valve 70 that prevents or significantly impedes the inflow of oil into ATS sump chamber 46, 48 under breach conditions. Oil feed shutoff valve 70 cannot be seen in FIG. 1 due to the location of the cross-section plane, but is described in detail below in conjunction with FIGS. 2 and 3.

Figure 2:
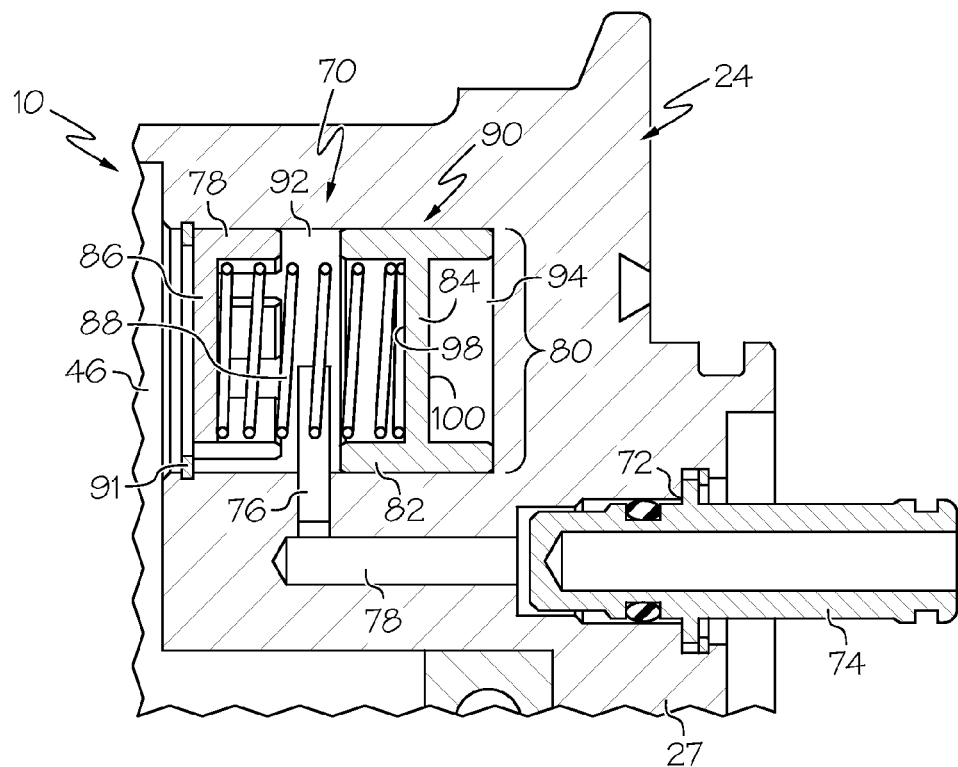
FIGS. 2 and 3 are cross-sectional views of a portion of the shared oil ATS shown in FIG. 1, as taken along different cross-section planes and further illustrating the exemplary oil feed shutoff valve in open and closed positions, respectively.
Figure 3:
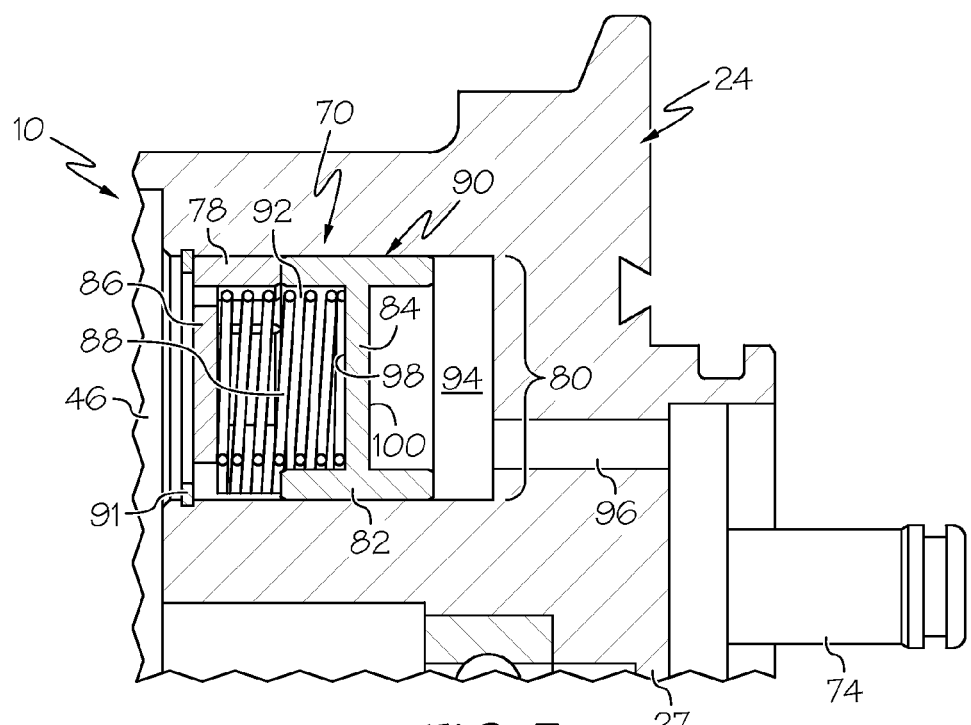

FIGS. 2 and 3 are cross-sectional views of ATS 10 (partially shown), as taken along cross section planes in which oil feed shutoff valve 70 is visible. In the exemplary embodiment shown in FIGS. 2 and 3, a fitting or "transfer tube" 74 is inserted into oil inlet 72 to allow ATS 10 to be supplied with a pressurized stream of engine oil. In other embodiments, different fluid connections can be utilized and the oil supplied to ATS 10 can be provided as a gravity fed spray, jet, or metered supply. It can further be seen that oil inlet 72 is not directly connected to sump chamber 46, 48 (FIG. 1), but rather fluidly coupled thereto through an oil flow passage 76, 78 and a valve cavity 80, which is provided in housing assembly 24. Stated differently, oil inlet 72 is fluidly coupled to sump chamber 46, 48 through valve cavity 80. Oil flow passage 76, 78 includes a circumferential channel or annular groove 76 (e.g., a fly cut), which extends at least partially around the outer circumferential surface of valve cavity 80. Additionally, oil flow passage 76, 78 includes a straight bore section 78, which fluidly connects oil inlet 72 to circumferential groove 76. Under normal operating conditions, oil feed shutoff valve 70 is maintained in an open position in which the valve element of shutoff valve 70 (annular sidewall 82 of below-described shuttle 90) leaves annular groove 76 unobstructed or uncovered. In the unlikely event of an ATS housing breach, however, the valve element of shutoff valve 70 moves to a position covering annular groove 76 to block oil flow into valve cavity 80 and, therefore, into sump chamber 46, 48. Oil feed shutoff valve 70 can assume any form suitable for providing this function, but preferably assumes the form of a shuttle valve having a cylindrical or annular valve element of the type described below.

In the exemplary embodiment shown in FIGS. 2 and 3, oil feed shutoff valve 70 includes the following major components: (i) a valve element 82, (ii) a piston 84, (iii) a cup-shaped spring retainer 86, and (iv) a compression spring 88. Valve element 82 and piston 84 are advantageously produced as a single (e.g., machined) piece or "shuttle" 90, although this need not be the case in all embodiments. Valve element 82 assumes the form of an annular sidewall included within shuttle 90, which selectively covers annular groove 78 of oil flow passage 76, 78 depending upon the translational position of shuttle 90. In further embodiments, valve element 82 can assume other forms, providing that element 82 can be moved to selectively obstruct or block engine oil flow through valve cavity 80 and into sump chamber 46, 48. When oil feed shutoff valve 70 is installed within ATS 10, shuttle 90 is first inserted into valve cavity 80, a first end of spring 88 is then placed in contact with shuttle 90, and spring retainer 86 is lastly positioned in contact with the opposing end of spring 88 and secured in place utilizing, for example, a lock ring 91.

Shuttle 90 can slide axially within valve cavity 80; the term "axially," as appearing herein, defined as a direction parallel to the centerline or rotational axis 34 of ATS 10 (FIG. 1). Shuttle 90 and, therefore, valve element 82 and piston 84 are movable between a first translational extreme (the open position shown in FIG. 2) and a second translational extreme (the closed position shown in FIG. 3). When shuttle 90 resides in the open position shown in FIG. 2, valve element 82 is axially offset from and does not cover circumferential groove 76 such that oil may flow freely from flow passage 76, 78 into sump 48. More specifically, when shuttle 90 (and therefore valve element 82) resides in the open position (FIG. 2), engine oil received through ATS oil inlet 72 flows through flow passage 76, 78; into valve cavity 80; through the openings provided in spring retainer 86; and into ATS sump chamber 46, 48 to refresh the oil reservoir contained within sump 48. Conversely, when shuttle 90 resides in the closed position shown in FIG. 3, valve element 82 blocks oil flow into valve cavity 80 through flow passage 76, 78, to prevent or substantially prevent the flow of engine oil into sump chamber 46, 48 of ATS 10. Due to the structural configuration of circumferential groove 76 and the annular sidewall 82 of shuttle 90, oil feed shutoff valve 70 is able to provide a complete or substantially complete seal when closed to substantially impeded, if not entirely prevent the inflow of oil into sump chamber 46, 48 under breach conditions.

Oil feed shutoff valve 70 further includes a control pressure chamber 92 and a reference pressure chamber 94, which are generally defined by valve cavity 80 and shuttle 90. Specifically, chambers 92 and 94 are circumferentially bound by the inner surface of cavity 80 and fluidly partitioned by shuttle 90. Control pressure chamber 92 is fluidly coupled to air cavity 46 of ATS sump chamber 46, 48 through a number of openings provided in spring retainer 86. Reference pressure chamber 94 is fluidly coupled to a reference pressure by a reference pressure duct 96 (shown in FIG. 3). Reference pressure duct 96 preferably intersects a bottom portion of reference pressure chamber 94 to promote the drainage of any engine oil, which leaks across shuttle 90 into chamber 94. In preferred embodiments, reference pressure duct 96 fluidly couples chamber 94 to the engine gearbox pad such that the reference pressure is the AGB pressure; that is, the pressure within AGB and the AGB pad on which ATS 10 is installed. The pressure within control pressure chamber 92 acts on a first face 98 of piston 84 and, thus, exerts a force urging movement of shuttle 90 toward the open position (FIG. 2). Compression spring 88 likewise biases shuttle 90 (and therefore piston 84 and valve element 82) toward the open position (FIG. 2). Conversely, the pressure within reference pressure chamber 94 acts on a second, opposing face 100 of piston 84 to exert an antagonistic force on shuttle 90 urging shuttle 90 toward the closed position (FIG. 3). Furthermore, in the illustrated example, piston faces 98 and 100 have substantially equivalent effective surface areas; although this need not always be the case. Under normal operating conditions during which the pressures within chambers 92 and 94 are substantially equivalent, the antagonistic pneumatic forces exerted on piston 84 cancel. Shuttle 90 is consequently maintained in the open position (FIG. 2) by the resilient bias force of spring 88.

The AGB pressure is equivalent or substantially equivalent to the pressure within air cavity 46 of ATS sump chamber 46, 48 under normal operating conditions. However, under breach conditions, the pressure within air cavity 46 decreases relative to the AGB pressure such that a pressure differential develops across piston 84 to urge movement of shuttle 90 toward the closed position (FIG. 3). When the force exerted on shuttle 90 by this pressure differential is sufficient to overcome the spring bias force, shuttle 90 slides toward the closed position (to the left in FIGS. 2 and 3) and valve element 82 blocks oil flow into valve cavity 80 through flow passage 76, 78. When shuttle 90 moves into the closed position (FIG. 3), valve element 82 blocks oil flow passage 76, 78 such that little to no oil flow is permitted to enter valve cavity 80 and ultimately flow into ATS sump chamber 46, 48. In this manner, valve element 82 and, more generally, shuttle 90 automatically moves into a closed position to quickly arrest oil loss from GTE 11 (FIG. 1) through ATS 10 in the event of an ATS housing breach. Notably, due to the manner in which annular sidewall 82 of shuttle 90 fully covers circumferential groove 76 (as seen from the interior of valve cavity 80), oil feed shutoff valve 70 provides high integrity seal in the closed position permitting very little, if any leakage across shuttle 90 when closed. The leakage of engine oil into ATS 10 under breach conditions is consequently greatly reduced, if not eliminated to more effectively prevent oil loss from GTE 11 (FIG. 1) in the unlikely event of an ATS housing breach.

Figure 4:
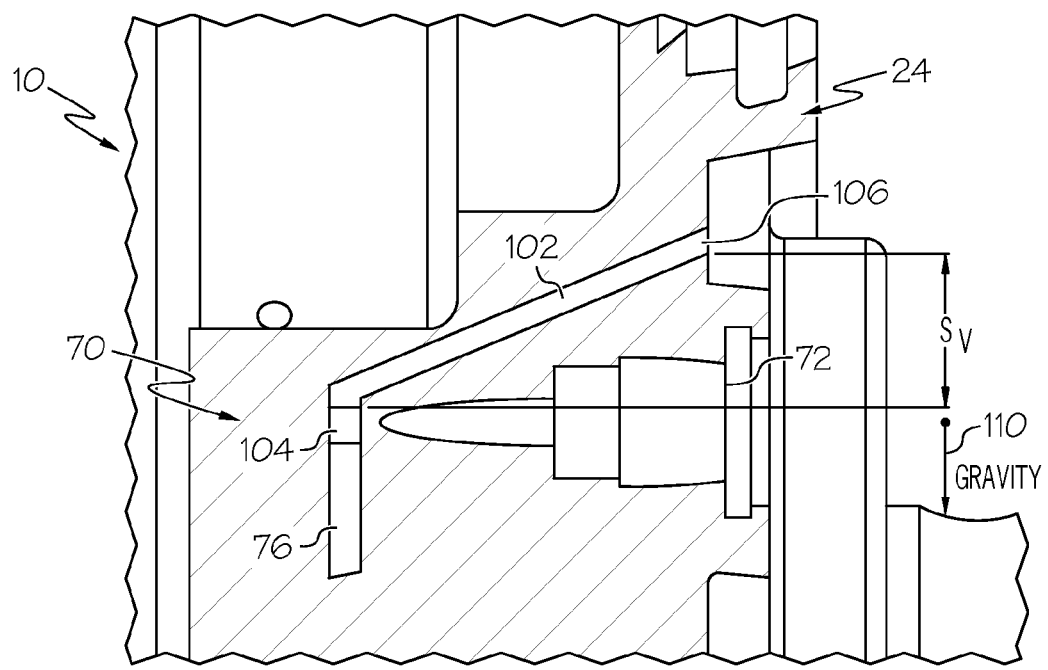
FIG. 4 is a cross-sectional view of the shared oil ATS shown in FIGS. 2 and 3 (partially shown), as taken along a still further cross-section plane to reveal a rejected oil return passage further included in the exemplary ATS.

FIG. 4 is a cross-sectional view of shared oil ATS 10 and shutoff valve 70, as taken along a different cross-section plane revealing a rejected oil return duct or passage 102 further included in ATS 10. A portion of circumferential groove 76 and oil inlet 72 can also been seen in FIG. 4. Rejected oil return passage 102 includes an inlet 104, which fluidly connects to a lower portion of groove 76, and an outlet 106, which provides fluid communication with the exterior of ATS 10. When shuttle 90 moves into the closed position (FIG. 3) such that oil flow into valve cavity 80 is generally prevented by valve element 82, oil flow is redirected from flow passage 74, 76 into rejected oil return passage 102. The rejected engine oil then flows through rejected oil return passage 102, exits via outlet 106, and returns to the oil flow circuit of GTE 11 and, therefore, to AGB 12 (FIG. 1). Undesirable pressure build-up of engine oil at valve element 82 and, more generally, shuttle 90 in the closed position is thus prevented. In this manner, rejected oil return passage 102 provides a dedicated return path for the rejected oil flow, with passage 102 being fluidly isolated or partitioned from reference pressure duct 96 (FIG. 3) by shuttle 90. Additionally, in the illustrated embodiment, rejected oil return passage 102 remains in fluid communication with circumferential groove 76 and, more generally, with flow passage 76, 78 regardless of the translational position of shuttle 90. As a result, some fraction of the engine oil supplied to ATS 10 may also be permitted to flow through rejected oil return passage 102 when shuttle 90 is in the open position should the oil level within oil feed shutoff valve 70 become undesirably high; that is, surpass a maximum oil level threshold set by the vertical elevation of outlet 106 relative to valve cavity 80.

Figure 5:
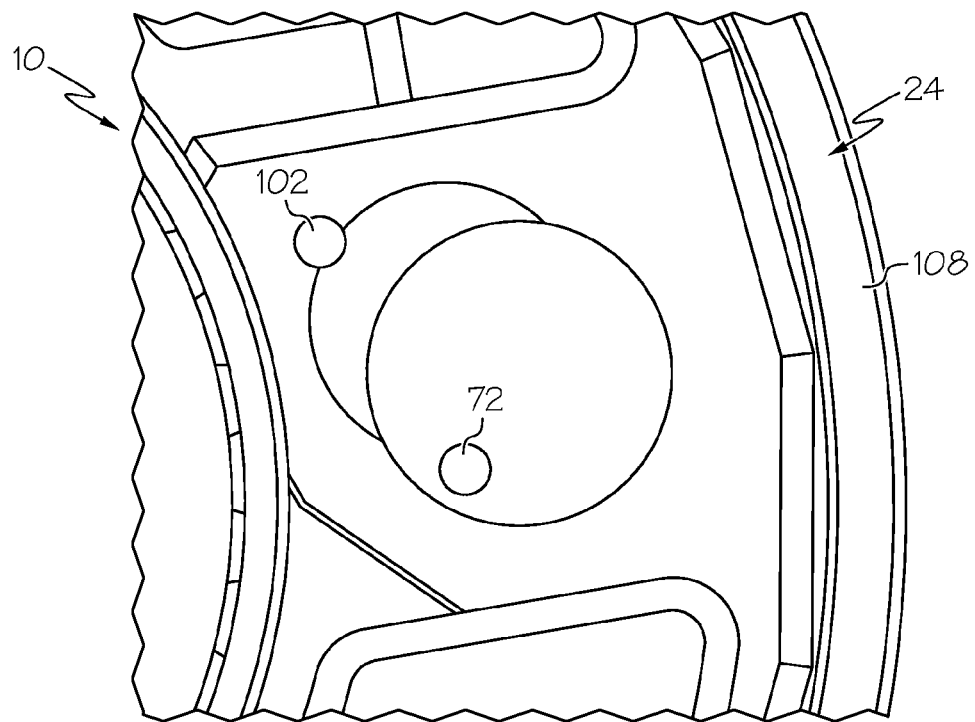
FIG. 5 is an isometric view of an end wall or plate included in the exemplary shared oil ATS shown in FIGS. 1-4 and more clearly illustrating the relative positioning of the ATS oil inlet and the rejected oil return passage.

The outlet 106 of rejected oil return passage 102 is preferably located above inlet 104 of passage 102 (and oil inlet port 72 of ATS 10) by a predetermined vertical distance or separation to prevent the flow of oil through passage 102 until such time as the oil level or pressure head within oil feed shutoff valve 70 surpasses a maximum acceptable threshold. This vertical separation is identified by double-headed arrow $S_V$ and is taken along a line parallel to the direction of gravity (represented in FIG. 4 by symbol 110). Stated differently, outlet 106 of return passage 102 is formed at a vertical elevation higher than that of inlet 104, with the term "vertical" defined as parallel to the direction of gravity when ATS 10 is installed on a gas turbine engine. This may be accomplished by forming rejected oil return passage 102 as an elongated channel or cross-bore angled with respect to a line parallel to the centerline of shutoff valve 70, as generally shown in FIG. 5. In one embodiment, $S_V$ is at least one half the diameter of valve cavity 80. In another embodiment, and as further shown in FIG. 4, rejected oil return passage 102 is formed such that oil inlet 104 connects to circumferential groove 76 at a location vertically below valve cavity 80, while oil outlet 106 is located at a vertical elevation overlapping with or above valve cavity 80. The relative positioning of rejected oil return passage 102 and flow passage 74, 76 is further illustrated in FIG. 5, which is an end view of a housing end plate 108 in which passage 102 and flow passage 74, 76 are formed (as seen from the interior of ATS 10).

The foregoing has thus provided embodiments of a shared oil ATS including an oil feed shutoff valve, which prevents or at least significantly reduces oil flow into the sump chamber of the ATS in the unlikely event of an ATS housing breach. In preferred embodiments, the oil feed shutoff valve is pressure actuated and shutoffs oil flow to the ATS in response to a decrease in an air cavity pressure of the ATS relative to the AGB pressure. Notably, and in contrast to certain conventionally-proposed oil feed shutoff valves, such as spring-loaded ball or stopper-type shutoff valves, the oil feed shutoff valve (e., shutoff valve 70 shown in FIGS. 2 and 3) provides complete or near complete blockage of oil supply to the ATS (e.g., ATS 10 shown in FIGS. 1-5) when closed to greatly reduce engine oil loss through the ATS under breach conditions. Additionally, in the above-described exemplary embodiment, the ATS further includes a dedicated rejected oil return passage, which directs oil back to the AGB when the shutoff valve is closed or when the oil level within the valve cavity surpasses a maximum level. In so doing, the rejected oil return passage minimizes pressure build-up upstream of the shutoff valve when closed. The inlet and outlet of the dedicated return passage are also orientated to prevent the undesired drainage of oil when the shutoff valve is in an open or partially-closed position and to provide a set head of oil urging the inflow of engine oil into the ATS sump chamber under non-breach conditions. The end result is a shared oil ATS including an oil feed shutoff valve providing superior control of engine oil loss through the ATS should an ATS housing breach occur.

The foregoing has also provided embodiments of a gas turbine engine including a shared oiled ATS having one or more oil loss control features. In one embodiment, the gas turbine engine includes an AGB containing an AGB pressure, as well as an ATS fluidly coupled to the AGB and configured to exchange oil therewith during engine operation. The ATS includes a housing having an oil inlet through which engine oil is received. A sump chamber is provided in the housing. The sump chamber retains a portion of the engine oil received through the oil inlet and contains an air cavity pressure. A pressure-actuated shutoff valve is fluidly coupled to the sump chamber. The pressure-actuated shutoff valve can be external to the ATS in some embodiments, but is preferably contained within the ATS and fluidly coupled between the sump chamber and the oil inlet of the ATS. The pressure-actuated shutoff valve is configured to block oil flow into the sump chamber in response to a decrease in the air cavity pressure relative to the AGB pressure. By automatically closing in response to such a decrease in these relative pressures, the oil feed shutoff valve quickly and effectively blocks oil flow into the ATS sump to prevent significant oil loss from the gas turbine engine, which could otherwise necessitate in-flight engine shutdown. Furthermore, the oil feed shutoff valve is advantageously implemented as a shuttle valve having an annular sidewall to provide a high integrity seal when in a closed position to greatly reduce, if not entirely prevent inflow of engine oil into the ATS under breach conditions. Additionally, a dedicated rejected oil return path can be provided to alleviate the accumulation of oil pressure upstream of the shutoff valve when closed; and/or to prevent the undesired drainage of oil when the shutoff valve is in an open or partially open position.

While multiple exemplary embodiments have been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention. It being understood that various changes may be made in the function and arrangement of elements described in an exemplary embodiment without departing from the scope of the invention as set-forth in the appended Claims.

What is claimed is:

1. An Air Turbine Starter (ATS), comprising:
   an ATS housing assembly having a sump chamber, an oil inlet, and a valve cavity fluidly coupled between the sump chamber and the oil inlet;
   a rejected oil return passage formed in the ATS housing assembly and fluidly coupled to the valve cavity;
   an oil feed shutoff valve positioned in the valve cavity and containing a valve element movable between: (i) an open position in which the valve element permits oil flow from the oil inlet, through the valve cavity, and into the sump chamber, and (ii) a closed position in which valve element blocks oil flow from the oil inlet into the sump chamber, while redirecting the oil flow into the rejected oil return passage; and
   a circumferential groove formed at least partially around the valve cavity, the circumferential groove fluidly coupled between the valve cavity and the oil inlet, the circumferential groove further fluidly coupled between the oil inlet and the rejected oil return passage.

2. The ATS of claim 1 wherein the rejected oil return passage comprises an inlet and an outlet, the outlet of the rejected oil return passage formed in the ATS housing assembly at a vertical elevation higher than the inlet of the rejected oil return passage.

3. The ATS of claim 2 wherein the ATS has a centerline, and wherein the rejected oil return passage comprises an elongated channel formed in the ATS housing assembly and angled with respect to a line parallel to the centerline of the ATS.

4. The ATS of claim 1 wherein the valve element comprises a cylindrical sidewall, which covers the circumferential groove when the valve element is in the closed position.

5. The ATS of claim 1 wherein the rejected oil return passage intersects a lower portion of the circumferential groove.

6. The ATS of claim 1 wherein the oil feed shutoff valve further comprises:
   a piston fixedly coupled to the valve element;
   a control pressure chamber at least partially defined by the piston and the valve cavity, the control pressure chamber containing a first pressure urging movement of the valve element toward the open position; and
   a reference pressure chamber at least partially defined by the piston and the valve cavity, the reference pressure chamber containing a second pressure urging movement of the valve element toward the closed position.

7. An Air Turbine Starter (ATS) configured to be installed within a gas turbine engine containing an Accessory Gearbox (AGB), the ATS comprising:
   an ATS housing assembly having a sump chamber, an oil inlet, and a valve cavity fluidly coupled between the sump chamber and the oil inlet;
   a rejected oil return passage formed in the ATS housing assembly and fluidly coupled to the valve cavity;
   an oil feed shutoff valve positioned in the valve cavity, the oil feed shutoff valve comprising:
     a valve element movable between: (i) an open position in which the valve element permits oil flow from the oil inlet, through the valve cavity, and into the sump chamber, and (ii) a closed position in which valve element blocks oil flow from the oil inlet into the sump chamber, while redirecting the oil flow into the rejected oil return passage;
     a piston fixedly coupled to the valve element;
     a control pressure chamber at least partially defined by the piston and the valve cavity, the control pressure chamber containing a first pressure urging movement of the valve element toward the open position; and
     a reference pressure chamber at least partially defined by the piston and the valve cavity, the reference pressure chamber containing a second pressure urging movement of the valve element toward the closed position; and
   a reference pressure duct formed in the ATS housing and fluidly coupling the reference pressure chamber to the AGB when the ATS is installed within the gas turbine engine.

8. The ATS of claim 7 wherein the reference pressure duct is fluidly isolated from the rejected oil return passage by the valve element.

9. The ATS of claim 7 wherein the reference pressure duct intersects a bottom portion of the reference pressure chamber to permit drainage of engine oil leakage from the reference pressure chamber.

10. The ATS of claim 7 wherein sump chamber comprises an air cavity containing an ATS air pressure, and wherein the oil feed shutoff valve control pressure chamber is fluidly coupled to the air cavity such that the first pressure is equivalent to the ATS air pressure.

11. An Air Turbine Starter (ATS) configured to be installed within an engine cavity, the ATS comprising:
   an ATS housing assembly containing a sump chamber and an oil inlet;
   a valve cavity fluidly coupled between the sump chamber and the oil inlet;
   a circumferential groove extending at least partially around the valve cavity;
   an oil feed shutoff valve positioned in the valve cavity and containing a valve element having an annular sidewall, the oil feed shutoff valve movable between open and closed positions in which the annular sidewall uncovers and covers the circumferential groove, respectively, to selectively obstruct oil flow from the oil inlet, through the circumferential groove, and into the sump chamber; and
   a rejected oil return passage fluidly coupled to the circumferential groove, the rejected oil return passage redirecting oil received at the oil inlet back to the engine cavity when the valve element is in the closed position.

12. The ATS of claim 11 wherein the ATS is configured to be installed within an engine cavity containing an Accessory Gearbox (AGB) pressure, wherein the sump chamber contains an air cavity pressure, wherein the oil feed shutoff valve moves from the open position to the closed position when the air cavity pressure decreases below the AGB pressure by a predetermined amount.

13. The ATS of claim 12 wherein the oil feed shutoff valve further comprises a piston fixedly coupled to the valve element and moving in conjunction therewith between open and closed positions, the piston comprising:
   a first face exposed to the air cavity pressure; and
   a second face opposite the first face and exposed to the AGB pressure.

14. The ATS of claim 11 wherein the rejected oil return passage is fluidly coupled to the oil inlet of the ATS housing assembly through the circumferential groove such that oil flow is permitted from the oil inlet, around a portion of the annular sidewall, and to the rejected oil return passage when the valve element is in the closed position.

15. The ATS of claim 11 wherein the rejected oil return passage comprises:
   an inlet formed in the ATS housing assembly; and
   an outlet fluidly coupled to the inlet of the rejected oil return passage, the outlet of the rejected oil return passage formed in the ATS housing assembly at a vertical elevation higher than the inlet of the rejected oil return passage such that a set head of oil urging the inflow of oil into the sump chamber is provided when the valve element is in the open position and the ATS operates under non-breach conditions.

16. The ATS of claim 11 wherein the engine cavity contains an Accessory Gearbox (AGB) pressure, and wherein the ATS further comprises:
   a reference pressure chamber; and
   a reference pressure duct formed in the ATS housing assembly and placing the reference pressure chamber in fluid communication with the AGB pressure when the ATS is installed within the gas turbine engine.

17. The ATS of claim 16 wherein the reference pressure duct is fluidly isolated from the rejected oil return passage by the valve element.

18. The ATS of claim 16 wherein the reference pressure duct intersects a bottom portion of the reference pressure chamber to permit drainage of engine oil leakage therefrom.

19. The ATS of claim 16 wherein the sump chamber comprises an air cavity containing an ATS air pressure, and wherein the ATS further comprises a control pressure chamber fluidly coupled to the ATS air pressure.

20. The ATS of claim 11 wherein the ATS has a centerline, and wherein the rejected oil return passage comprises an elongated channel formed in the ATS housing assembly and angled with respect to a line parallel to the centerline of the ATS.

* * * * *